United States Patent [19]
Zones et al.

[11] Patent Number: 5,958,370
[45] Date of Patent: Sep. 28, 1999

[54] ZEOLITE SSZ-39

[75] Inventors: Stacey I. Zones, San Francisco; Yumi Nakagawa, Oakland; Susan T. Evans, Mountain View; Gregory S. Lee, San Ramon, all of Calif.

[73] Assignee: Chevron U.S.A. Inc., San Francisco, Calif.

[21] Appl. No.: 08/988,723

[22] Filed: Dec. 11, 1997

Related U.S. Application Data

[60] Provisional application No. 60/033,955, Dec. 31, 1996.

[51] Int. Cl.$^6$ .......................... C01B 39/06; C01B 39/12; C01B 39/48
[52] U.S. Cl. .......................... 423/706; 423/712; 423/713; 423/718; 423/212; 423/239.2; 208/27; 208/58; 208/59; 208/111.01; 208/120.01; 585/533; 585/666; 585/671; 585/700; 585/640; 585/733; 95/130
[58] Field of Search ...................... 423/706, 718, 423/713, 212, 239.2, 712; 208/27, 58, 59, 111.01, 120.01; 585/533, 666, 671, 700, 640, 733; 95/130

[56] References Cited

U.S. PATENT DOCUMENTS

| | | | |
|---|---|---|---|
| 5,187,132 | 2/1993 | Zones et al. | 502/64 |
| 5,254,514 | 10/1993 | Nakagawa | 423/718 |
| 5,273,736 | 12/1993 | Nakagawa | 423/706 |
| 5,316,753 | 5/1994 | Nakagawa | 423/706 |
| 5,340,563 | 8/1994 | Zones et al. | 423/706 |
| 5,397,560 | 3/1995 | Millar et al. | 423/718 |
| 5,580,540 | 12/1996 | Nakagawa | 423/718 |
| 5,645,812 | 7/1997 | Nakagawa | 423/706 |
| 5,785,947 | 7/1998 | Zones et al. | 423/706 |

FOREIGN PATENT DOCUMENTS

| | | |
|---|---|---|
| 95/09812 | 4/1995 | WIPO . |
| 96/34827 | 11/1996 | WIPO . |

*Primary Examiner*—Mark L. Bell
*Assistant Examiner*—David Sample
*Attorney, Agent, or Firm*—Richard J. Sheridan

[57] ABSTRACT

The present invention relates to new crystalline zeolite SSZ-39 prepared using a cyclic or polycyclic quaternary ammonium cation templating agent.

40 Claims, No Drawings

ZEOLITE SSZ-39

This application claims the benefit of U.S. Provisional Application 60/033,955 filed Dec. 31, 1996.

BACKGROUND OF THE INVENTION

1. Field of the Invention

The present invention relates to new crystalline zeolite SSZ-39, a method for preparing SSZ-39 using a variety of cyclic and polycyclic quaternary ammonium cation templating agents, and processes employing SSZ-39 as a catalyst.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications. New zeolites may contain novel internal pore architectures, providing enhanced selectivities in these processes.

Crystalline aluminosilicates are usually prepared from aqueous reaction mixtures containing alkali or alkaline earth metal oxides, silica, and alumina. Crystalline borosilicates are usually prepared under similar reaction conditions except that boron is used in place of aluminum. By varying the synthesis conditions and the composition of the reaction mixture, different zeolites can often be formed.

SUMMARY OF THE INVENTION

The present invention is directed to a family of crystalline molecular sieves with unique properties, referred to herein as "zeolite SSZ-39" or simply "SSZ-39". Preferably, SSZ-39 is obtained in its silicate, aluminosilicate, titanosilicate, vanadosilicate or borosilicate form. The term "silicate" refers to a zeolite having a high mole ratio of silicon oxide relative to aluminum oxide, preferably a mole ratio greater than 100. As used herein, the term "aluminosilicate" refers to a zeolite containing both alumina and silica and the term "borosilicate" refers to a zeolite containing oxides of both boron and silicon.

In accordance with this invention, there is also provided a zeolite having a mole ratio greater than about 10 of an oxide of a first tetravalent element to an oxide of a second tetravalent element different from said first tetravalent element, trivalent element, pentavalent element or mixture thereof and having, after calcination, the X-ray diffraction lines of Table II.

Further, in accordance with this invention, there is provided a zeolite having a mole ratio greater than about 10 of an oxide selected from silicon oxide, germanium oxide and mixtures thereof to an oxide selected from aluminum oxide, gallium oxide, iron oxide, boron oxide, titanium oxide, indium oxide, vanadium oxide and mixtures thereof and having, after calcination, the X-ray diffraction lines of Table II below.

The present invention further provides such a zeolite having a composition, as synthesized and in the anhydrous state, in terms of mole ratios as follows:

$YO_2/W_cO_d$ 10–100
$M_{2/n}/YO_2$ 0.01–0.03
$Q/YO_2$ 0.02–0.05 wherein Y is silicon, germanium or a mixture thereof; W is aluminum, gallium, iron, boron, titanium, indium, vanadium or mixtures thereof; c is 1 or 2; d is 2 when c is 1 (i.e., W is tetravalent) or d is 3 or 5 when c is 2 (i.e., d is 3 when W is trivalent or 5 when W is pentavalent); M is an alkali metal cation, alkaline earth metal cation or mixtures thereof; n is the valence of M (i.e., 1 or 2); and Q is at least one cyclic and polycyclic quaternary ammonium cation.

In accordance with this invention, there is also provided a zeolite prepared by thermally treating a zeolite having a mole ratio of an oxide selected from silicon oxide, germanium oxide and mixtures thereof to an oxide selected from aluminum oxide, gallium oxide, iron oxide, boron oxide, titanium oxide, indium oxide, vanadium oxide and mixtures thereof greater than about 10 at a temperature of from about 200° C. to about 800° C., the thus-prepared zeolite having the X-ray diffraction lines of Table II. The present invention also includes this thus-prepared zeolite which is predominantly in the hydrogen form, which hydrogen form is prepared by ion exchanging with an acid or with a solution of an ammonium salt followed by a second calcination.

Also provided in accordance with the present invention is a method of preparing a crystalline material comprising an oxide of a first tetravalent element and an oxide of a second tetravalent element which is different from said first tetravalent element, trivalent element, pentavalent element or mixture thereof, said method comprising contacting under crystallization conditions sources of said oxides and a templating agent comprising a cyclic or polycyclic quaternary ammonium cation.

The present invention additionally provides a process for converting hydrocarbons comprising contacting a hydrocarbonaceous feed at hydrocarbon converting conditions with a catalyst comprising the zeolite of this invention. The zeolite may be predominantly in the hydrogen form. It may also be substantially free of acidity.

Further provided by the present invention is a hydrocracking process comprising contacting a hydrocarbon feedstock under hydrocracking conditions with a catalyst comprising the zeolite of this invention, preferably predominantly in the hydrogen form.

This invention also includes a dewaxing process comprising contacting a hydrocarbon feedstock under dewaxing conditions with a catalyst comprising the zeolite of this invention, preferably predominantly in the hydrogen form.

Also included in the present invention is a process for preparing a lubricating oil which comprises hydrocracking in a hydrocracking zone a hydrocarbonaceous feedstock to obtain an effluent comprising a hydrocracked oil, and catalytically dewaxing said effluent comprising hydrocracked oil at a temperature of at least about 400° F. and at a pressure of from about 15 psig to about 3000 psig in the presence of added hydrogen gas with a catalyst comprising at least one Group VIII metal and the zeolite of this invention. The zeolite may be predominantly in the hydrogen form.

Also provided by the present invention is a catalytic cracking process comprising contacting a hydrocarbon feedstock in a reaction zone under catalytic cracking conditions in the absence of added hydrogen with a catalyst comprising the zeolite of this invention, preferably predominantly in the hydrogen form. Also included in this invention is such a catalytic cracking process wherein the catalyst additionally comprises a large pore crystalline cracking component.

The present invention also includes a process for oligomerizing olefins comprising contacting an olefin feed under oligomerization conditions with a catalyst comprising the zeolite of this invention.

There is further provided in accordance with this invention a process for isomerizing olefins comprising contacting an olefin feed under isomerization conditions with a catalyst comprising the zeolite of this invention.

Further provided in accordance with this invention is a process for the production of higher molecular weight hydrocarbons from lower molecular weight hydrocarbons comprising the steps of:

(a) introducing into a reaction zone a lower molecular weight hydrocarbon-containing gas and contacting said gas in said zone under $C_{2+}$ hydrocarbon synthesis conditions with a catalyst comprising the zeolite of this invention and a metal or metal compound capable of converting the lower molecular weight hydrocarbon to a higher molecular weight hydrocarbon; and (b) withdrawing from said reaction zone a higher molecular weight hydrocarbon-containing stream. Preferably, the metal or metal compound is a lanthanide or actinide metal or metal compound and the lower molecular weight hydrocarbon is methane.

This invention also provides a process for converting lower alcohols and other oxygenated hydrocarbons comprising contacting said lower alcohol or other oxygenated hydrocarbon with a catalyst comprising the zeolite of this invention under conditions to liquid products.

Also provided by the present invention is an improved process for the reduction of oxides of nitrogen contained in a gas stream in the presence of oxygen wherein said process comprises contacting the gas stream with a zeolite, the improvement comprising using as the zeolite a zeolite having a mole ratio greater than about 10 of an oxide of a first tetravalent element to an oxide of a second tetravalent element different from said first tetravalent element, trivalent element, pentavalent element or mixture thereof and having, after calcination, the X-ray diffraction lines of Table II. The zeolite may contain a metal or metal ions (such as cobalt, copper or mixtures thereof) capable of catalyzing the reduction of the oxides of nitrogen, and may be conducted in the presence of a stoichiometric excess of oxygen. In a preferred embodiment, the gas stream is the exhaust stream of an internal combustion engine.

Also provided in accordance with this invention is a process for the separation of nitrogen from a nitrogen-containing gas mixture comprising contacting the mixture with a composition comprising the zeolite of this invention. In a preferred embodiment, the gas mixture contains nitrogen and methane.

DETAILED DESCRIPTION OF THE INVENTION

The present invention comprises a family of crystalline, highly constrained pore zeolites designated herein "zeolite SSZ-39" or simply "SSZ-39". As used herein, the term "highly constrained pore" means having an average pore size diameter less than about 5.0 Angstroms, preferably from about 3.5 Angstroms to about 4.0 Angstroms.

In preparing SSZ-39 zeolites, a cyclic or polycyclic quaternary ammonium cation is used as a crystallization template. In general, SSZ-39 is prepared by contacting an active source of one or more oxides selected from the group consisting of monovalent element oxides, divalent element oxides, trivalent element oxides, and tetravalent element oxides with the cyclic or polycyclic quaternary ammonium cation templating agent.

SSZ-39 is prepared from a reaction mixture having the composition shown in Table A below.

TABLE A

| | Reaction Mixture | |
|---|---|---|
| | Typical | Preferred |
| $YO_2/W_aO_b$ | 10–100 | 15–60 |
| $OH^-/YO_2$ | 0.5–1.0 | 0.6–0.8 |
| $Q/YO_2$ | 0.05–0.50 | 0.10–0.20 |
| $M_{2/n}/YO_2$ | 0.30–1.0 | 0.50–0.60 |
| $H_2O/YO_2$ | 20–80 | 30–40 | where Y, W, Q, M and n are as defined above, and a is 1 or 2, and b is 2 when a is 1 (i.e., W is tetravalent) and b is 3 when a is 2 (i.e., W is trivalent).

In practice, SSZ-39 is prepared by a process comprising:

(a) preparing an aqueous solution containing sources of at least one oxide capable of forming a crystalline molecular sieve and a cyclic or polycyclic quaternary ammonium cation having an anionic counterion which is not detrimental to the formation of SSZ-39;

(b) maintaining the aqueous solution under conditions sufficient to form crystals of SSZ-39; and (c) recovering the crystals of SSZ-39.

Accordingly, SSZ-39 may comprise the crystalline material and the templating agent in combination with metallic and non-metallic oxides bonded in tetrahedral coordination through shared oxygen atoms to form a cross-linked three dimensional crystal structure. The metallic and non-metallic oxides comprise one or a combination of oxides of a first tetravalent element(s), and one or a combination of a second tetravalent element(s) different from the first tetravalent element(s), trivalent element(s), pentavalent element(s) or mixture thereof The first tetravalent element(s) is preferably selected from the group consisting of silicon, germanium and combinations thereof More preferably, the first tetravalent element is silicon. The second tetravalent element (which is different from the first tetravalent element), trivalent element and pentavalent element is preferably selected from the group consisting of aluminum, gallium, iron, boron, titanium, indium, vanadium and combinations thereof More preferably, the second trivalent or tetravalent element is aluminum or boron.

Typical sources of aluminum oxide for the reaction mixture include aluminates, alumina, aluminum colloids, aluminum oxide coated on silica sol, hydrated alumina gels such as $Al(OH)_3$ and aluminum compounds such as $AlCl_3$ and $Al_2(SO_4)_3$. Typical sources of silicon oxide include silicates, silica hydrogel, silicic acid, fumed silica, colloidal silica, tetra-alkyl orthosilicates, and silica hydroxides. Boron, as well as gallium, germanium, titanium, indium, vanadium and iron, can be added in forms corresponding to their aluminum and silicon counterparts.

A source zeolite reagent may provide a source of aluminum or boron. In most cases, the source zeolite also provides a source of silica. The source zeolite in its dealuminated or deboronated form may also be used as a source of silica, with additional silicon added using, for example, the conventional sources listed above. Use of a source zeolite reagent as a source of alumina for the present process is more completely described in U.S. Pat. No. 4,503,024 issued on Mar. 5, 1985 to Bourgogne et al. entitled "PROCESS FOR THE PREPARATION OF SYNTHETIC ZEOLITES, AND ZEOLITES OBTAINED BY SAID PROCESS", the disclosure of which is incorporated herein by reference. Dealuminated Y zeolite, LZ-210, is a particularly useful source.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The templating agent may be used to provide hydroxide ion. Thus, it may be beneficial to ion exchange, for example, the halide for hydroxide ion, thereby reducing or eliminating the alkali metal hydroxide quantity required. The alkali metal cation or alkaline earth cation may be part of the as-synthesized crystalline oxide material, in order to balance valence electron charges therein.

The reaction mixture is maintained at an elevated temperature until the crystals of the SSZ-39 zeolite are formed. The hydrothermal crystallization is usually conducted under autogenous pressure, at a temperature between 100° C. and 200° C., preferably between 135° C. and 160° C. The crystallization period is typically greater than 1 day and preferably from about 3 days to about 20 days.

Preferably, the zeolite is prepared using mild stirring or agitation.

During the hydrothermal crystallization step, the SSZ-39 crystals can be allowed to nucleate spontaneously from the reaction mixture. The use of SSZ-39 crystals as seed material can be advantageous in decreasing the time necessary for complete crystallization to occur. In addition, seeding can lead to an increased purity of the product obtained by promoting the nucleation and/or formation of SSZ-39 over any undesired phases. When used as seeds, SSZ-39 crystals are added in an amount between 0.1 and 10% of the weight of silica used in the reaction mixture.

Once the zeolite crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-39 zeolite crystals. The drying step can be performed at atmospheric pressure or under vacuum.

SSZ-39 as prepared has a mole ratio of an oxide selected from silicon oxide, germanium oxide and mixtures thereof to an oxide selected from aluminum oxide, gallium oxide, iron oxide, boron oxide, titanium oxide, indium oxide, vanadium oxide and mixtures thereof greater than about 10; and has the X-ray diffraction lines of Table I below. SSZ-39 further has a composition, as synthesized and in the anhydrous state, in terms of mole ratios, shown in Table B below.

TABLE B

| As-Synthesized SSZ-39 | |
| --- | --- |
| $YO_2/W_cO_d$ | 10–100 |
| $M_{2/n}/YO_2$ | 0.01–0.03 |
| $Q/YO_2$ | 0.02–0.05 | where Y, W, c, d, M and Q are as defined above.

SSZ-39 can be made essentially aluminum free, i.e., having a silica to alumina mole ratio of ∞. A method of increasing the mole ratio of silica to alumina is by using standard acid leaching or chelating treatments. SSZ-39 can be synthesized directly only as an aluminosilicate.

It is believed that SSZ-39 is comprised of a new framework structure or topology which is characterized by its X-ray diffraction pattern. SSZ-39 zeolites, as-synthesized, have a crystalline structure whose X-ray powder diffraction pattern exhibit the characteristic lines shown in Table I and is thereby distinguished from other known zeolites.

TABLE I

| As-Synthesized SSZ-39 | | |
| --- | --- | --- |
| 2 Theta[a] | d | Relative Intensity[b] |
| 9.55 | 9.25 | VS |
| 10.65 | 8.30 | W |
| 16.15 | 5.48 | VS |
| 17.05 | 5.20 | VS |
| 17.30 | 5.12 | VS |
| 20.7 | 4.29 | S |
| 21.5 | 4.13 | M |
| 24.1 | 3.69 | M |
| 28.5 | 3.18 | M |
| 31.6 | 2.86 | M |

[a] ±0.3
[b] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

After calcination, the SSZ-39 zeolites have a crystalline structure whose X-ray powder diffraction pattern include the characteristic lines shown in Table II:

TABLE II

| Calcined SSZ-39 | | |
| --- | --- | --- |
| 2 Theta[a] | d | Relative Intensity |
| 9.55 | 9.25 | VS |
| 10.65 | 8.30 | M |
| 16.15 | 5.48 | M |
| 17.05 | 5.20 | M |
| 17.30 | 5.12 | M |
| 20.70 | 4.29 | M |
| 21.50 | 4.13 | M |
| 24.10 | 3.69 | M |
| 28.05 | 3.18 | W |
| 31.3 | 2.86 | W |

[a] ±0.3

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.30 degrees.

The X-ray diffraction pattern of Table I is representative of "as-synthesized" or "as-made" SSZ-39 zeolites. Minor variations in the diffraction pattern can result from variations in the silica-to-alumina or silica-to-boron mole ratio of the particular sample due to changes in lattice constants. In addition, sufficiently small crystals will affect the shape and intensity of peaks, leading to significant peak broadening.

Representative peaks from the X-ray diffraction pattern of calcined SSZ-39 are shown in Table II. Calcination can also result in changes in the intensities of the peaks as compared to patterns of the "as-made" material, as well as minor shifts in the diffraction pattern. The zeolite produced by exchanging the metal or other cations present in the zeolite with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

Crystalline SSZ-39 can be used as-synthesized, but preferably will be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica to alumina mole ratio. The zeolite can also be steamed; steaming helps stabilize the crystalline lattice to attack from acids.

The zeolite can be used in intimate combination with hydrogenating components, such as tungsten, vanadium molybdenum, rhenium, nickel cobalt, chromium, manganese, or a noble metal, such as palladium or platinum, for those applications in which a hydrogenation-dehydrogenation function is desired.

Metals may also be introduced into the zeolite by replacing some of the cations in the zeolite with metal cations via standard ion exchange techniques (see, for example, U.S. Pat. Nos. 3,140,249 issued Jul. 7, 1964 to Plank et al.; 3,140,251 issued Jul. 7, 1964 to Plank et al.; and 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the SSZ-39. The zeolite can also be impregnated with the metals, or, the metals can be physically and intimately admixed with the zeolite using standard methods known to the art.

Typical ion-exchange techniques involve contacting the synthetic zeolite with a solution containing a salt of the desired replacing cation or cations. Although a wide variety of salts can be employed, chlorides and other halides, acetates, nitrates, and sulfates are particularly preferred. The zeolite is usually calcined prior to the ion-exchange procedure to remove the organic matter present in the channels and on the surface, since this results in a more effective ion exchange. Representative ion exchange techniques are disclosed in a wide variety of patents including U.S. Pat. Nos. 3,140,249 issued on Jul. 7, 1964 to Plank et al.; 3,140,251 issued on Jul. 7, 1964 to Plank et al.; and 3,140,253 issued on Jul. 7, 1964 to Plank et al.

Following contact with the salt solution of the desired replacing cation, the zeolite is typically washed with water and dried at temperatures ranging from 65° C. to about 200° C. After washing, the zeolite can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of SSZ-39, the spatial arrangement of the atoms which form the basic crystal lattice of the zeolite remains essentially unchanged.

SSZ-39 can be formed into a wide variety of physical shapes. Generally speaking, the zeolite can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded.

SSZ-39 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

Hydrocarbon Conversion Processes

SSZ-39 zeolites are useful in hydrocarbon conversion reactions. Hydrocarbon conversion reactions are chemical and catalytic processes in which carbon containing compounds are changed to different carbon containing compounds. Examples of hydrocarbon conversion reactions in which SSZ-39 are expected to be useful include hydrocracking, dewaxing, catalytic cracking, and olefin and aromatics formation reactions. The catalysts are also expected to be useful in other petroleum refining and hydrocarbon conversion reactions such as polymerizing and oligomerizing olefinic or acetylenic compounds such as isobutylene and butene-1, and oxidation reactions, and isomerizing olefins. Also included are rearrangement reactions to make various naphthalene derivatives, and forming higher molecular weight hydrocarbons from lower molecular weight hydrocarbons (e.g., methane upgrading). The SSZ-39 catalysts may have high selectivity, and under hydrocarbon conversion conditions can provide a high percentage of desired products relative to total products.

SSZ-39 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, synthetic paraffins from NAO, recycled plastic feedstocks and, in general, can be any carbon containing feedstock susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

The following table indicates typical reaction conditions which may be employed when using catalysts comprising SSZ-39 in the hydrocarbon conversion reactions of this invention. Preferred conditions are indicated in parentheses.

| Process | Temp., ° C. | Pressure | LHSV |
|---|---|---|---|
| Hydrocracking | 175–485 | 0.5–350 bar | 0.1–30 |
| Dewaxing | 200–475 | 15–3000 psig | 0.1–20 |
|  | (250–450) | (200–3000) | (0.2–10) |
| Cat. cracking | 127–885 | subatm.$^{-1}$ | 0.5–50 |
|  |  | (atm.–5 atm.) |  |

-continued

| Process | Temp., °C | Pressure | LHSV |
|---|---|---|---|
| Oligomerization | 232–649[2] | 0.1–50 atm.[2,3] | 0.2–50[2] |
|  | 10–232[4] | — | 0.05–20[5] |
|  | (27–204)[4] | — | (0.1–10)[5] |
| Condensation of alcohols | 260–538 | 0.5–1000 psig | 0.5–50[5] |

[1]Several hundred atmospheres
[2]Gas phase reaction
[3]Hydrocarbon partial pressure
[4]Liquid phase reaction
[5]WHSV Other reaction conditions and parameters are provided below.

Hydrocracking

Using a catalyst which comprises SSZ-39, preferably predominantly in the hydrogen form, and a hydrogenation promoter, heavy petroleum residual feedstocks, cyclic stocks and other hydrocrackate charge stocks can be hydrocracked using the process conditions and catalyst components disclosed in the aforementioned U.S. Pat. No. 4,910,006 and U.S. Pat. No. 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium rhodium, iridium, ruthenium and mixtures thereof or the group consisting of at least one of nickel, molybdenum, cobalt, tungsten, titanium, chromium and mixtures thereof Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, and preferably in the range of from 0.05 to 25% by weight.

Dewaxing

SSZ-39, preferably predominantly in the hydrogen form, can be used to dewax hydrocarbonaceous feeds by selectively removing straight chain paraffins. Typically, the viscosity index of the dewaxed product is improved (compared to the waxy feed) when the waxy feed is contacted with SSZ-39 under isomerization dewaxing conditions.

The catalytic dewaxing conditions are dependent in large measure on the feed used and upon the desired pour point. Hydrogen is preferably present in the reaction zone during the catalytic dewaxing process. The hydrogen to feed ratio is typically between about 500 and about 30,000 SCF/bbl (standard cubic feet per barrel), preferably about 1000 to about 20,000 SCF/bbl. Generally, hydrogen will be separated from the product and recycled to the reaction zone. Typical feedstocks include light gas oil, heavy gas oils and reduced crudes boiling above about 350° F.

A typical dewaxing process is the catalytic dewaxing of a hydrocarbon oil feedstock boiling above about 350° F. and containing straight chain and slightly branched chain hydrocarbons by contacting the hydrocarbon oil feedstock in the presence of added hydrogen gas at a hydrogen pressure of about 15–3000 psi with a catalyst comprising SSZ-39 and at least one Group VIII metal.

The SSZ-39 hydrodewaxing catalyst may optionally contain a hydrogenation component of the type commonly employed in dewaxing catalysts. See the aforementioned U.S. Pat. No. 4,910,006 and U.S. Pat. No. 5,316,753 for examples of these hydrogenation components.

The hydrogenation component is present in an effective amount to provide an effective hydrodewaxing and hydroisomerization catalyst preferably in the range of from about 0.05 to 5% by weight. The catalyst may be run in such a mode to increase isodewaxing at the expense of cracking reactions.

The feed may be hydrocracked, followed by dewaxing. This type of two stage process and typical hydrocracking conditions are described in U.S. Pat. No. 4,921,594, issued May 1, 1990 to Miller, which is incorporated herein by reference in its entirety.

SSZ-39 may also be used to dewax raffinates, including bright stock, under conditions such as those disclosed in U.S. Pat. No. 4,181,598, issued Jan. 1, 1980 to Gillespie et al., which is incorporated by reference herein in its entirety.

It is often desirable to use mild hydrogenation (sometimes referred to as hydrofinishing) to produce more stable dewaxed products. The hydrofinishing step can be performed either before or after the dewaxing step, and preferably after. Hydrofinishing is typically conducted at temperatures ranging from about 190° C. to about 340° C. at pressures from about 400 psig to about 3000 psig at space velocities (LHSV) between about 0.1 and 20 and a hydrogen recycle rate of about 400 to 1500 SCF/bbl. The hydrogenation catalyst employed must be active enough not only to hydrogenate the olefins, diolefins and color bodies which may be present, but also to reduce the aromatic content. Suitable hydrogenation catalyst are disclosed in U.S. Pat. No. 4,921,594, issued May 1, 1990 to Miller, which is incorporated by reference herein in its entirety. The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Lube oil may be prepared using SSZ-39. For example, a $C_{20+}$ lube oil may be made by isomerizing a $C_{20}$ + olefin feed over a catalyst comprising SSZ-39 in the hydrogen form and at least one Group VIII metal. Alternatively, the lubricating oil may be made by hydrocracking in a hydrocracking zone a hydrocarbonaceous feedstock to obtain an effluent comprising a hydrocracked oil, and catalytically dewaxing the effluent at a temperature of at least about 400° F. and at a pressure of from about 15 psig to about 3000 psig in the presence of added hydrogen gas with a catalyst comprising SSZ-39 in the hydrogen form and at least one Group VIII metal.

Catalytic Cracking

Hydrocarbon cracking stocks can be catalytically cracked in the absence of hydrogen using SSZ-39, preferably predominantly in the hydrogen form.

When SSZ-39 is used as a catalytic cracking catalyst in the absence of hydrogen, the catalyst may be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. No. 4,910,006 and U.S. Pat. No. 5,316,753. When a traditional cracking catalyst (TC) component is employed, the relative weight ratio of the TC to the SSZ-39 is generally between about 1:10 and about 500:1, desirably between about 1:10 and about 200:1, preferably between about 1:2 and about 50:1, and most preferably is between about 1:1 and about 20:1. The novel zeolite and/or the traditional cracking component may be further ion exchanged with rare earth ions to modify selectivity.

The cracking catalysts are typically employed with an inorganic oxide matrix component. See the aforementioned U.S. Pat. No. 4,910,006 and U.S. Pat. No. 5,316,753 for examples of such matrix components.

Oligomerization

It is expected that SSZ-39 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous or liquid phase with a catalyst comprising SSZ-39.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20% by weight. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens et al. which is incorporated totally herein by reference. If required, such zeolites may be obtained by steaming, by use in a conversion process or by any other method which may occur to one skilled in this art.

Isomerization of Olefins

SSZ-39 can be used to isomerize olefins. The feed stream is a hydrocarbon stream containing at least one $C_{4-6}$ olefin, preferably a $C_{4-6}$ normal olefin, more preferably normal butene. Normal butene as used in this specification means all forms of normal butene, e.g., 1-butene, cis-2-butene, and trans-2-butene. Typically, hydrocarbons other than normal butene or other $C_{4-6}$ normal olefins will be present in the feed stream. These other hydrocarbons may include, e.g., alkanes, other olefins, aromatics, hydrogen, and inert gases.

The feed stream typically may be the effluent from a fluid catalytic cracking unit or a methyl-tert-butyl ether unit. A fluid catalytic cracking unit effluent typically contains about 40–60 weight percent normal butenes. A methyl-tert-butyl ether unit effluent typically contains 40–100 weight percent normal butene. The feed stream preferably contains at least about 40 weight percent normal butene, more preferably at least about 65 weight percent normal butene. The terms iso-olefin and methyl branched iso-olefin may be used interchangeably in this specification.

The process is carried out under isomerization conditions. The hydrocarbon feed is contacted in a vapor phase with a catalyst comprising the SSZ-39. The process may be carried out generally at a temperature from about 625° F. to about 950° F. (329–510° C.), for butenes, preferably from about 700° F. to about 900° F. (371–482° C.), and about 350° F. about 650° F. (177–343° C.) for pentenes and hexenes. The pressure ranges from subatmospheric to about 200 psig, preferably from about 15 psig to about 200 psig, and more preferably from about 1 psig to about 150 psig.

The liquid hourly space velocity during contacting is generally from about 0.1 to about 50 $hr^{-1}$, based on the hydrocarbon feed, preferably from about 0.1 to about 20 $hr^{-1}$, more preferably from about 0.2 to about 10 $hr^{-1}$, most preferably from about 1 to about 5 $hr^{-1}$. A hydrogen/hydrocarbon molar ratio is maintained from about 0 to about 30 or higher. The hydrogen can be added directly to the feed stream or directly to the isomerization zone. The reaction is preferably substantially free of water, typically less than about two weight percent based on the feed. The process can be carried out in a packed bed reactor, a fixed bed, fluidized bed reactor, or a moving bed reactor. The bed of the catalyst can move upward or downward. The mole percent conversion of, e.g., normal butene to iso-butene is at least 10, preferably at least 25, and more preferably at least 35.

Methane Upgrading

Higher molecular weight hydrocarbons can be formed from lower molecular weight hydrocarbons by contacting the lower molecular weight hydrocarbon with a catalyst comprising SSZ-39 and a metal or metal compound capable of converting the lower molecular weight hydrocarbon to a higher molecular weight hydrocarbon. Examples of such reactions include the conversion of methane to $C_{2+}$ hydrocarbons such as ethylene or benzene or both. Examples of useful metals and metal compounds include lanthanide and or actinide metals or metal compounds.

These reactions, the metals or metal compounds employed and the conditions under which they can be run are disclosed in U.S. Pat. Nos. 4,734,537, issued Mar. 29, 1988 to Devries et al.; 4,939,311, issued Jul. 3, 1990 to Washecheck et al.; 4,962,261, issued Oct. 9, 1990 to Abrevaya et al.; 5,095,161, issued Mar. 10, 1992 to Abrevaya et al.; 5,105,044, issued Apr. 14, 1992 to Han et al.; 5,105,046, issued Apr. 14, 1992 to Washecheck; 5,238,898, issued Aug. 24, 1993 to Han et al.; 5,321,185, issued Jun. 14, 1994 to van der Vaart; and 5,336,825, issued Aug. 9, 1994 to Choudhary et al., each of which is incorporated herein by reference in its entirety.

Condensation of Alcohols

SSZ-39 can be used to condense lower aliphatic alcohols having 1 to 10 carbon atoms to a gasoline boiling point hydrocarbon product comprising mixed aliphatic and olefinic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Other Uses for SSZ-39

SSZ-39 can also be used as an adsorbent with high selectivities based on molecular sieve behavior and also based upon preferential hydrocarbon packing within the pores.

SSZ-39 may also be used for the catalytic reduction of the oxides of nitrogen in a gas stream. Typically, the gas stream also contains oxygen, often a stoichiometric excess thereof. Also, the SSZ-39 may contain a metal or metal ions within or on it which are capable of catalyzing the reduction of the nitrogen oxides. Examples of such metals or metal ions include copper, cobalt and mixtures thereof.

One example of such a process for the catalytic reduction of oxides of nitrogen in the presence of a zeolite is disclosed in U.S. Pat. No. 4,297,328, issued Oct. 27, 1981 to Ritscher et al., which is incorporated by reference herein. There, the catalytic process is the combustion of carbon monoxide and hydrocarbons and the catalytic reduction of the oxides of nitrogen contained in a gas stream, such as the exhaust gas from an internal combustion engine. The zeolite used is metal ion-exchanged, doped or loaded sufficiently so as to provide an effective amount of catalytic copper metal or copper ions within or on the zeolite. In addition, the process is conducted in an excess of oxidant, e.g., oxygen.

SSZ-39 may also be used in the separation of gases, such as the separation of nitrogen from a nitrogen-containing gas mixture. One example of such separation is the separation of nitrogen from methane (e.g., the separation of nitrogen from natural gas).

EXAMPLES

The following examples demonstrate but do not limit the present invention. The templating agents indicated in Table C below are used in these examples.

TABLE C

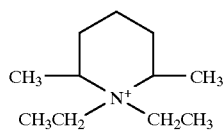

N,N-Diethyl-2,6-dimethylpiperidinium cation
(Template A)

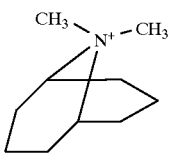

N,N-Dimethyl-9-azoniabicyclo[3.3.1]nonane
(Template B)

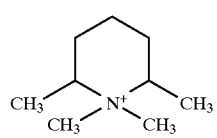

N,N-Dimethyl-2,6-dimethylpiperidinium cation
(Template C)

TABLE C-continued

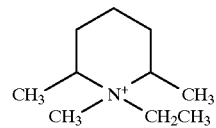

N-Ethyl-N-methyl-2,6-dimethylpiperidinium cation
(Template D)

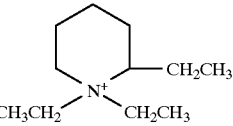

N,N-Diethyl-2-ethylpiperidinium cation
(Template E)

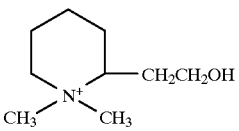

N,N-Dimethyl-2-(2-hydroxyethyl)piperidinium cation
(Template F)

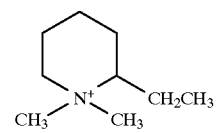

N,N-Dimethyl-2-ethylpiperidinium cation
(Template G)

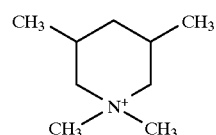

N,N-Dimethyl-3,5-dimethylpiperidinium cation
(Template H)

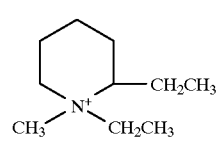

N-Ethyl-N-methyl-2-ethylpiperidinium cation
(Template I)

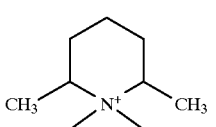

2,6-Dimethyl-1-Azonium[5.4]decane cation
(Template J)

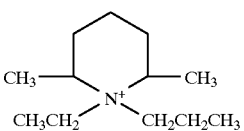

N-Ethyl-N-propyl-2,6-dimethylpiperidinium cation
(Template K)

TABLE C-continued

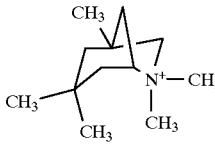

2,2,4,6,6-Pentamethyl-2-azoniabicyclo[3.2.1]octane cation
(Template L)

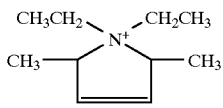

N,N-Diethyl-2,5-dimethyl-2,5-dihydropyrrolium cation
(Template M)

The anion (X⁻) associated with the cation may be any anion which is not detrimental to the formation of the zeolite. Representative anions include halogen, e.g., fluoride, chloride, bromide and iodide, hydroxide, acetate, sulfate, tetrafluoroborate, carboxylate, and the like. Hydroxide is the most preferred anion.

Example 1

Synthesis of N,N-diethyl-cis-2,6-dimethylpiperidinium Hydroxide (Template A)

Thirty-six grams of cis-2,6-dimethylpiperidine is mixed with 320 ml of methanol and 64 grams of potassium bicarbonate. Ethyl iodide (199 grams) is added dropwise to the reaction mixture and, following complete addition, the reaction mixture is heated at reflux for three days. Following isolation of the desired product, the salt is recrystallized from hot acetone and ether with a small amount of methanol and the iodide salt is converted to the hydroxide salt by treatment with Bio-Rad AG1-X8 anion exchange resin. The hydroxide ion concentration is determined by titration of the resulting solution using phenolphthalein as the indicator.

Example 2

Synthesis of SSZ-39

Four grams of a solution of Template A (0.56 mmol OH⁻/g) is mixed with 6.1 grams of water and 0.20 grams of 1.0 N NaOH. Ammonium exchanged Y zeolite (0.25 gram) is added to this solution and, finally, 2.5 gram of Banco "N" sodium silicate (28–29 wt. % $SiO_2$) is added. The resulting reaction mixture is sealed in a Parr 4745 reactor and heated at 135° C. and rotated at 43 rpm. After seven days, a settled product is obtained and determined by XRD to be SSZ-39. Analysis of this product shows the $SiO_2/Al_2O_3$ mole ratio to be 14.7.

Examples 3–14

The following examples use the templates described in Table C above and use the same ratios of reactants as shown in Example 2. Higher silica/alumina mole ratios can be obtained by using LZ-210 as the alumina source in the reaction (LZ-210 silica/alumina mole ratio=13.) In all Examples, the product is crystalline SSZ-39.

TABLE D

| Example No. | Template | Al Source | Days | Product(s) |
|---|---|---|---|---|
| 3 | B | $NH_4^+$—Y (Y62) | 6 | SSZ-39 |
| 4 | C | " | 6 | SSZ-39 |
| 5 | D | " | 6 | SSZ-39 |
| 6 | E | " | 6 | SSZ-39 |
| 7 | F | " | 13 | SSZ-39, small amount of mordenite |
| 8 | G | " | 6 | SSZ-39* |
| 9 | H | " | 8 | SSZ-39 |
| 10 | I | " | 9 | SSZ-39* |
| 11 | J | " | 8 | SSZ-39* |
| 12 | K | " | 7 | SSZ-39* |
| 13 | L | Na—Y (Y52) | 14 | SSZ-39 |
| 14 | M | $NH_4^+$—Y (Y62) | 7 | SSZ-39 |

*Minor analcime product

Example 15

The reaction as described in Example 3 is repeated, with the exception of using 0.14 gram of Y-62 in the reaction mixture. This results in a silica/alumina mole ratio in the reaction mixture of 67. After six days at 170° C. (43 rpm) a product is isolated and determined to by XRD to be SSZ-39.

Example 16

The reaction described in Example 3 is repeated, with the exception that 0.08 gram of Y62 is used. This results in a starting silica/alumina mole ratio of 100. After five days at 135° C. and 43 rpm, a product was isolated and determined by XRD to be SSZ-39. The product is analyzed and found to have a silica/alumina mole ratio of 51. The X-ray diffraction data is shown in Table III below.

TABLE III

| 2 Theta | d | $I/I_0 \times 100$ |
|---|---|---|
| 9.6 | 9.21 | 100 |
| 10.7 | 8.24 | 12 |
| 12.95 | 6.83 | 11 |
| 13.6 | 6.51 | 1 |
| 14.1 | 6.27 | 10 |
| 14.95 | 5.92 | 21 |
| 16.20 | 5.47 | 91 |
| 17.15 | 5.17 | 84 |
| 17.4 | 5.09 | 86 |
| 19.2 | 4.62 | 7 |
| 19.8 | 4.48 | 28 |
| 20.3 | 4.37 | 28 |
| 20.75 | 4.28 | 56 |
| 21.3(Sh) | 4.17 | 9 |
| 21.6 | 4.11 | 37 |
| 22.25 | 3.99 | 5 |
| 23.35 | 3.80 | 2 |
| 24.15 | 3.68 | 40 |
| 25.4 | 3.50 | 4 |
| 26.1 | 3.41 | 25 |
| 26.65 | 3.34 | 25 |
| 27.4 | 3.25 | 2 |
| 27.9(Sh) | 3.19 | 6 |
| 28.2 | 3.16 | 21 |
| 29.7 | 3.00 | 7 |
| 30.2 | 2.96 | 15 |
| 30.6(Sh) | 2.92 | 7 |
| 30.8 | 2.90 | 9 |
| 31.4 | 2.85 | 33 |
| 32.1 | 2.79 | 5 |
| 32.6 | 2.75 | 16 |
| 33.15 | 2.70 | 9 |
| 33.95 | 2.64 | 2 |

TABLE III-continued

| 2 Theta | d | I/I₀ × 100 |
|---|---|---|
| 34.75 | 2.58 | 3 |
| 35.1 | 2.55 | 2 |
| 35.75 | 2.51 | 1 |
| 36.4(Sh) | 2.47 | 2 |
| 36.75 | 2.44 | 4 |
| 37.1(Sh) | 2.42 | 2 |
| 39.3(Sh) | 2.29 | 1 |
| 39.65 | 2.27 | 3 |
| 40.65 | 2.22 | 2 |
| 41.65 | 2.17 | 3 |

Example 17

The material from Example 2 was calcined in the following manner. A thin bed of material was heated in a muffle furnace from room temperature to 120° C. at a rate of 1° C. per minute and held at 120° C. for three hours. The temperature was then ramped up to 540° C. at the same rate and held at this temperature for 5 hours, after which it was increased to 594° C. and held there for another 5 hours. A 50/50 mixture of air and nitrogen was passed over the zeolite at a rate of 20 standard cubic feet per minute during heating.

Example 18

Using Template L as the iodide salt, 4 grams of this material is mixed with 40 grams of water, 20 grams of 1N NaOH, and 26.84 grams of Banco "N" silicate (sodium silicate). 2.50 Grams of LZ-210 is added as a source of Al. The resulting mixture is heated at 130° C. without stirring until sampling electron microscopy analysis shows that a new crystalline phase has emerged, and that all of the LZ-210 has been consumed. The product is determined to be SSZ-39. After calcination as in Example 17, the XRD pattern for the calcined SSZ-39 is that tabulated in Table IV below. The product has a silica/alumina mole ratio of 17.1.

TABLE IV

| 2 Theta | d | I/I₀ × 100 |
|---|---|---|
| 9.50 | 9.29 | 100 |
| 10.6 | 8.32 | 25 |
| 12.9 | 6.84 | 15 |
| 13.5 | 6.56 | 5 |
| 14.0 | 6.33 | 2 |
| 14.8 | 5.99 | 2 |
| 16.1 | 5.50 | 20 |
| 17.0 | 5.22 | 29 |
| 17.25 | 5.14 | 33 |
| 19.1 | 4.64 | 5 |
| 19.7 | 4.50 | 10 |
| 20.1 | 4.41 | 8 |
| 20.7 | 4.28 | 26 |
| 21.25(Sh) | 4.18 | 11 |
| 21.4 | 4.15 | 22 |
| 22.6 | 3.93 | 1 |
| 23.2 | 3.83 | 5 |
| 24.0 | 3.70 | 29 |
| 25.3 | 3.52 | 4 |
| 26.0 | 3.43 | 6 |
| 26.4 | 3.37 | 13 |
| 27.95 | 3.19 | 13 |
| 28.2(Sh) | 3.16 | 4 |
| 29.4 | 3.04 | 2 |
| 29.75 | 3.00 | 2 |
| 30.1 | 2.96 | 7 |
| 30.5 | 2.93 | 7 |
| 30.9(Sh) | 2.89 | 2 |

TABLE IV-continued

| 2 Theta | d | I/I₀ × 100 |
|---|---|---|
| 31.3 | 2.86 | 17 |
| 31.8 | 2.81 | 3 |
| 32.35 | 2.77 | 10 |
| 32.9 | 2.72 | 5 |
| 33.2(Sh) | 2.70 | 2 |
| 33.9 | 2.64 | 1 |
| 34.45 | 2.60 | 1 |

Example 19

Ion exchange of calcined SSZ-39 material (prepared in Example 17) is performed using $NH_4NO_3$ to convert the zeolite from its $Na^+$ form to the $NH_4^+$ form, and, ultimately, the $H^+$ form. Typically, the same mass of $NH_4NO_3$ as zeolite is slurried in water at a ratio of 25–50:1 water to zeolite. The exchange solution is heated at 95° C. for 2 hours and then filtered. This procedure can be repeated up to four times. Following the final exchange, the zeolite was washed several times with water and dried. This $NH_{4+}$ form of SSZ-39 can then be converted to the $H^+$ form by calcination (as described in Example 17) to 540° C. The product is subjected to a surface area and micropore volume analysis using $N_2$ as adsorbate and via the BET method. The surface area of the zeolitic material is 597 $M^2/g$ and the micropore volume is 0.275 cc/g.

Example 20

The hydrogen form of the zeolite of Example 18 (after treatment according to Examples 17 and 19) is pelletized at 2–3 KPSI, crushed and meshed to 20–40, and then >0.50 gram is calcined at about 540° C. in air for four hours and cooled in a desiccator. 0.50 Gram is packed into a ⅜ inch stainless steel tube with alundum on both sides of the zeolite bed. A Lindburg furnace is used to heat the reactor tube. Helium is introduced into the reactor tube at 10 cc/min. and at atmospheric pressure. The reactor is heated to about 315° C., and a 50/50 (w/w) feed of n-hexane and 3-methylpentane is introduced into the reactor at a rate of 8 µl/min. Feed delivery is made via a Brownlee pump. Direct sampling into a gas chromatograph begins after 10 minutes of feed introduction. The Constraint Index value is calculated from the gas chromatographic data using methods known in the art, and is found to be >30.

It can be seen that SSZ-39 has very high cracking activity, indicative of strongly acidic sites. The high C.I. of >30 shows a preference for cracking the linear n-hexane over the branched alkane (3-methylpentane), which is behavior typical of small-pore zeolites.

Example 21

The hydrogen form of the zeolite of Example 2 (after treatment according to Examples 17 and 19) is pelletized at 2–3 KPSI, then crushed and meshed to 20–40. 0.50 Gram is loaded into a ⅜ inch stainless steel reactor tube with alundum on the side of the zeolite bed where the feed is introduced. The reactor is heated in a Lindberg furnace to 1000° F. for 3 hours in air, and then the temperature is reduced to 400° C. in a stream of nitrogen at 20 cc/min. A 22.1% methanol feed (22.1 g methanol/77.9 g water) is introduced into the reactor at a rate of 1.31 cc/hr. The conversion at 10 minutes is 100%, and after 4 hours is still greater than 95%.

SSZ-39 makes very little liquid product and produces considerable light gas under these conditions. A large proportion of product is due to the formation of olefins (see Table E below). Product values are for 35 minutes on stream, 100% conversion.

TABLE E

| Product | Wt. % |
| --- | --- |
| Methane | 0.66 |
| Ethane | 1.56 |
| Ethylene | 20.76 |
| Propylene | 35.15 |
| Propane | 21.76 |
| Butenes/butanes | 13.64 |
| $C_5$ and larger | 5.50 |

It can be seen that $C_2$–$C_4$ accounts for greater than 90% of the product.

What is claimed is:

1. A zeolite having a mole ratio greater than about 10 of an oxide of a first tetravalent element to an oxide of a second tetravalent element which is different from said first tetravalent element, trivalent element, pentavalent element or mixture thereof and having, after calcination, the X-ray diffraction lines of Table II.

2. A zeolite having a mole ratio greater than about 10 of an oxide selected from the group consisting of silicon oxide, germanium oxide and mixtures thereof to an oxide selected from aluminum oxide, gallium oxide, iron oxide, boron oxide, titanium oxide, indium oxide, vanadium oxide and mixtures thereof, and having, after calcination, the X-ray diffraction lines of Table II.

3. A zeolite according to claim 2 wherein the oxides comprise silicon oxide and aluminum oxide.

4. A zeolite according to claim 1 wherein said zeolite is predominantly in the hydrogen form.

5. A zeolite according to claim 1 wherein said zeolite is substantially free of acidity.

6. A zeolite having a composition, as synthesized and in the anhydrous state, in terms of mole ratios as follows:

$YO_2/W_cO_d$ 10–100

$M_{2/n}/YO_2$ 0.01–0.03

$Q/YO_2$ 0.02–0.05 wherein Y is silicon, germanium or a mixture thereof; W is aluminum, gallium, iron, boron, titanium, indium, vanadium or mixtures thereof; c is 1 or 2; d is 2 when c is 1 or d is 3 or 5 when c is 2; M is an alkali metal cation, alkaline earth metal cation or mixtures thereof; n is the valence of M; and Q is at least one cyclic and polycyclic quaternary ammonium cation, said as-synthesized zeolite having the X-ray diffraction lines of Table I.

7. A zeolite according to claim 6 wherein W is aluminum and Y is silicon.

8. The zeolite according to claim 6 wherein Q has the following structure:

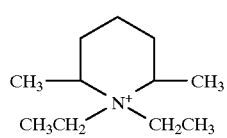

-continued

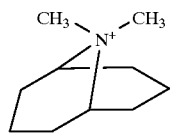

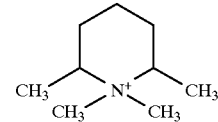

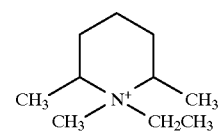

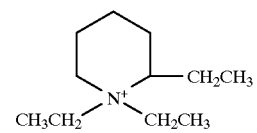

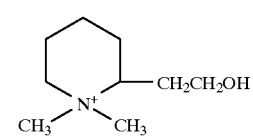

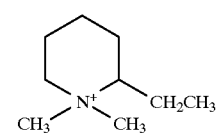

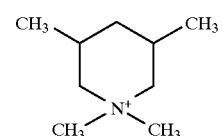

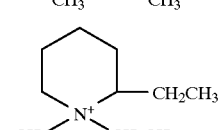

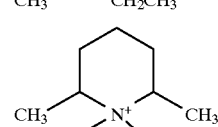

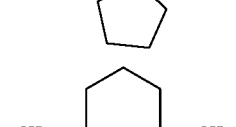

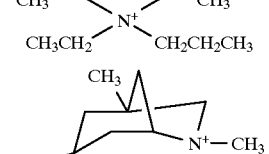

or

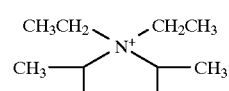

9. A method of preparing a crystalline material comprising an oxide of a first tetravalent element and an oxide of a second tetravalent element which is different from said first tetravalent element, trivalent element, pentavalent element or mixture thereof and having, after calcination, the X-ray diffraction lines of Table II, said method comprising contacting under crystallization conditions sources of said oxides and a templating agent comprising a cyclic or polycyclic quaternary ammonium cation.

10. The method according to claim 9 wherein the first tetravalent element is selected from the group consisting of silicon, germanium and combinations thereof.

11. The method according to claim 9 wherein the second tetravalent element, trivalent element or pentavalent element is selected from the group consisting of aluminum, gallium, iron, boron, titanium, indium, vanadium and combinations thereof.

12. The method according to claim 11 wherein the second tetravalent element or trivalent element is selected from the group consisting of aluminum, boron, titanium and combinations thereof.

13. The method according to claim 12 wherein the first tetravalent element is silicon.

14. The method according to claim 9 wherein the templating agent has the following structure:

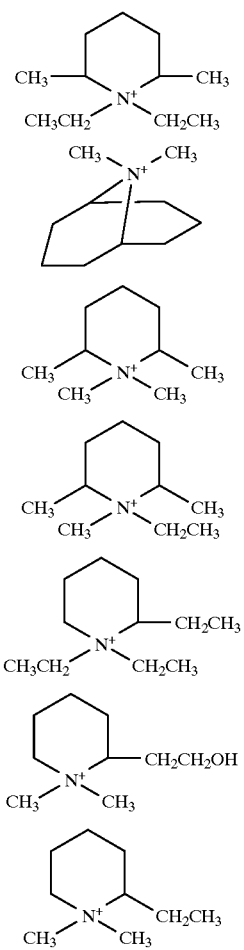

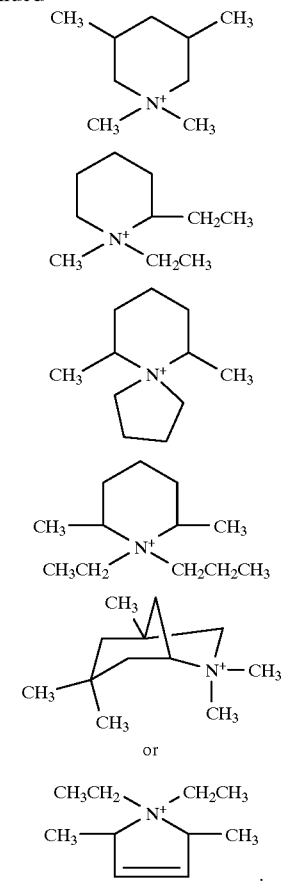

15. A process for converting hydrocarbons comprising contacting a hydrocarbonaceous feed at hydrocarbon converting conditions with a catalyst comprising a zeolite having a mole ratio greater than about 10 of an oxide of a first tetravalent element to an oxide of a second tetravalent element which is different from said first tetravalent element, trivalent element, pentavalent element or mixture thereof and having, after calcination, the X-ray diffraction lines of Table II.

16. The process of claim 15 wherein the zeolite is predominantly in the hydrogen form.

17. The process of claim 15 wherein the zeolite is substantially free of acidity.

18. The process of claim 15 wherein the process is a hydrocracking process comprising contacting the catalyst with a hydrocarbon feedstock under hydrocracking conditions.

19. The process of claim 18 wherein the zeolite is predominantly in the hydrogen form.

20. The process of claim 15 wherein the process is a dewaxing process comprising contacting the catalyst with a hydrocarbon feedstock under dewaxing conditions.

21. The process of claim 20 wherein the zeolite is predominantly in the hydrogen form.

22. The process of claim 15 wherein the process is a process for preparing a lubricating oil which comprises:
hydrocracking in a hydrocracking zone a hydrocarbonaceous feedstock to obtain an effluent comprising a hydrocracked oil; and
catalytically dewaxing said effluent comprising hydrocracked oil at a temperature of at least about 400° F. and at a pressure of from about 15 psig to about 3000 psig in the presence of added hydrogen gas with the catalyst.

23. The process of claim 22 wherein the zeolite is predominantly in the hydrogen form.

24. The process of claim 22 wherein the catalyst further comprises at least one Group VIII metal.

25. The process of claim 15 wherein the process is a catalytic cracking process comprising contacting a hydrocarbon feedstock in a reaction zone under catalytic cracking conditions in the absence of added hydrogen with the catalyst.

26. The process of claim 25 wherein the zeolite is predominantly in the hydrogen form.

27. The process of claim 25 wherein the catalyst additionally comprises a large pore crystalline cracking component.

28. The process of claim 15 wherein the process is a process for oligomerizing olefins comprising contacting an olefin feed under oligomerization conditions with the catalyst.

29. The process of claim 15 wherein the process is a process for isomerizing olefins comprising contacting an olefin feed under isomerization conditions with the catalyst.

30. The process of claim 29 wherein the olefin feed comprises at least one $C_4$–$C_6$ normal olefin.

31. The process of claim 15 wherein the process is a process for the production of higher molecular weight hydrocarbons from lower molecular weight hydrocarbons comprising the steps of:

(a) introducing into a reaction zone a lower molecular weight hydrocarbon-containing gas and contacting said gas in said zone under $C_{2+}$ hydrocarbon synthesis conditions with the catalyst and a metal or metal compound capable of converting the lower molecular weight hydrocarbon to a higher molecular weight hydrocarbon; and (b) withdrawing from said reaction zone a higher molecular weight hydrocarbon-containing stream.

32. The process of claim 31 wherein the metal or metal compound comprises a lanthanide or actinide metal or metal compound.

33. The process of claim 31 wherein the lower molecular weight hydrocarbon is methane.

34. A process for converting lower alcohols and other oxygenated hydrocarbons comprising contacting said lower alcohol or other oxygenated hydrocarbon under conditions to produce liquid products with a catalyst comprising a zeolite having a mole ratio greater than about 10 of an oxide of a first tetravalent element to an oxide of a second tetravalent element which is different from said first tetravalent element, trivalent element, pentavalent element or mixture thereof and having, after calcination, the X-ray diffraction lines of Table II.

35. In a process for the reduction of oxides of nitrogen contained in a gas stream in the presence of oxygen wherein said process comprises contacting the gas stream with a zeolite, the improvement comprising using as the zeolite a zeolite having a mole ratio greater than about 10 of an oxide of a first tetravalent element to an oxide of a second tetravalent element which is different from said first tetravalent element, trivalent element, pentavalent element or mixture thereof and having, after calcination, the X-ray diffraction lines of Table II.

36. The process of claim 35 wherein said zeolite contains a metal or metal ions capable of catalyzing the reduction of the oxides of nitrogen.

37. The process of claim 36 wherein the metal is copper, cobalt or mixtures thereof.

38. The process of claim 36 wherein the gas stream is the exhaust stream of an internal combustion engine.

39. A process for the separation of nitrogen from a nitrogen-containing gas mixture comprising contacting the mixture with a composition comprising a zeolite having a mole ratio greater than about 10 of an oxide of a first tetravalent element to an oxide of a second tetravalent element which is different from said first tetravalent element, trivalent element, pentavalent element or mixture thereof and having, after calcination, the X-ray diffraction lines of Table II.

40. The process of claim 39 wherein the gas mixture contains methane.

* * * * *